United States Patent [19]

Sills et al.

[11] 4,359,575
[45] Nov. 16, 1982

[54] PROCESS FOR TRIMERIZING ISOCYANIC ACID TO MAKE CYANURIC ACID

[75] Inventors: Ronald A. Sills, Cherry Hill, N.J.; Daniel S. Katz; Balwant Singh, both of Stamford, Conn.

[73] Assignee: American Cyanamid Company, Stamford, Conn.

[21] Appl. No.: 265,743

[22] Filed: May 21, 1981

Related U.S. Application Data

[63] Continuation-in-part of Ser. No. 128,000, Mar. 5, 1980, abandoned, which is a continuation-in-part of Ser. No. 58,219, Jul. 16, 1979, abandoned.

[51] Int. Cl.$^3$ ............................................. C07D 251/32
[52] U.S. Cl. ..................................................... 544/192
[58] Field of Search ......................................... 544/192

[56] References Cited

U.S. PATENT DOCUMENTS

| 2,822,363 | 2/1958 | Christmann et al. | 544/192 |
|---|---|---|---|
| 2,872,447 | 2/1959 | Oehlschlaeger | 544/192 |
| 3,065,233 | 11/1962 | Hopkins et al. | 544/192 |
| 3,297,697 | 1/1967 | Reynolds et al. | 544/192 |

FOREIGN PATENT DOCUMENTS

| 578398 | 6/1959 | Canada | 544/192 |
|---|---|---|---|
| 630288 | 10/1961 | Canada | 544/192 |
| 1053852 | 1/1967 | United Kingdom | 544/192 |

OTHER PUBLICATIONS

Redemann et al., Ind. & Chem. Eng., vol. 50, pp. 633–636 (1958).
Allied Chemical Product Bulletin, Apr. 9, 1959, "Cyanuric Acid" p. 2.

Primary Examiner—John M. Ford
Attorney, Agent, or Firm—Steven J. Hultquist

[57] ABSTRACT

Isocyanic acid is trimerized to cyanuric acid by contacting the isocyanic acid with liquid organic solvent, preferably polar solvent having high dielectric constant. The product is recovered as precipitate of good purity. Conversion and yield are high.

15 Claims, No Drawings

PROCESS FOR TRIMERIZING ISOCYANIC ACID TO MAKE CYANURIC ACID

This is a continuation-in-part of our copending application Ser. No. 128,000 filed Mar. 5, 1980 and now abandoned, which was a continuation-in-part of and copending with our application Ser. No. 058,219 filed July 16, 1979 and now abandoned.

The invention relates to manufacture of cyanuric acid by trimerizing isocyanic acid.

The prior art industrial methods for manufacture of cyanuric acid involved treatment of urea with heat. When heated, urea first melts and then solidifies but the conversion to cyanuric acid requires additional heating which is complicated by poor heat transfer in the solid mass, by loss of yield at excessive temperature, and by difficulty of removing solid products which adhere to reactor walls. The finished product mass often will contain impurities in amounts high enough to require further steps for purification. An object of the invention is to provide a process for manufacture of cyanuric acid from isocyanic acid with the highest attainable selectivity of conversion to cyanuric acid and hence the least production of by-product, particularly cyamelide.

According to the invention we contact isocyanic acid with a liquid organic solvent which will absorb isocyanic acid but from which the cyanuric acid product can be readily precipitated.

The trimerization reaction proceeds rapidly as the isocyanic acid is absorbed and the insoluble cyanuric acid product precipitates. Separation of the solid product is easily accomplished by settling or filtration or centrifuge or any suitable means for liquid-solids separation. Cyamelide; urea and other solid by-products also precipitate and are separated from the liquid reaction medium with the cyanuric acid product. This complicates the cyanuric acid purification and so in this process we are doubly interested to maximize the selectivity of conversion to cyanuric acid, not only to obtain maximum product yield but also to simplify, or eliminate the need for, product purification.

In the prior art, the trimerization of cyanic or isocyanic acid has been known at least since about 1885-6 when P. Klason described the reactions at J. Pract. Chem. [2] 33, 116-132. Klason suggested that anhydrous cyanic acid would polymerize to cyamelide while cyanic acid in solution would polymerize to cyanuric acid.

For the purpose of describing this invention we use the terms isocyanic acid and HNCO to include either isomer, cyanic acid or isocyanic acid, or mixtures thereof. In most cases the feed mixture will actually comprise an equilibrium mixture of the two isomers. The invention produces the best yields when the feed and the liquid solvent are both anhydrous.

In 1920 Werner and Fearon at Journ. Chem. Soc. 117, 1356, polymerized liquid cyanic acid at several temperatures from 0° C. to 20° C. to demonstrate increase of cyanuric acid conversion as temperature was increased.

W. Kern et al at Makromol. Chem. 14, 146-155 (1954) described polymerization at 15° C. of cyanic acid in benzene at several concentrations and suggested use of catalysts for the reaction. The reaction mixtures were prepared by pouring liquid cyanic acid into liquid benzene. The proportion of cyamelide in the product mixture ranged from 20% to 50%, increasing as the percent conversion was increased.

By way of contrast with prior art trimerization processes, the present invention can produce a cyanuric acid product of better than 90% purity and in some embodiments up to about 98-99 percent purity, together with high cyanic acid conversions, sometimes greater than 90%.

The results we obtain differ in several respects from results that were obtained by Kern, who mixed isocyanic acid liquid with benzene at low temperature and gradually increased the temperature to 15° C. In the presence of accelerators, e.g. tertiary amines, the polymerization of liquid cyanic acid in benzene as described by Kern, took place violently at 15° C. In the present process the reaction is not violent when accelerators are used. The polymerization is rapid and it is exothermic, but it can be easily controlled. Kern obtained higher percent conversions to cyamelide as the total percent conversions of cyanic acid were increased. We can obtain very high conversion rates while maintaining the selectivity of conversion to cyanuric acid at values over ninety percent.

The invention can be carried out using any of a number of organic solvents as the liquid medium for the polymerization, but we have found that some organic solvents are more conducive than others to the object of high selectivity of conversion. We prefer to use polar solvents and there is definite indication of a correlation between the dielectric constant of the solvent and the purity of the cyanuric acid product. In the detailed examples below the increase of product purity observed using several solvents of increasing dielectric constants is described. Purity over 90 percent was obtained consistently using several polar solvents having dielectric constants above 15. Purities over 80% were obtained consistently using solvents having dielectric constants greater than 5. It is preferable to have no water in the isocyanic acid feed or in the liquid solvent used for the invention. At present the most preferred liquid solvent appears to be acetonitrile. We would prefer, however, to use higher boiling liquids to minimize loss by vaporization in the gas-liquid contacting.

The invention is conveniently carried out at ordinary room temperatures. The trimerization reaction is exothermic and will heat the liquid solvent so that some cooling of the medium may be desirable. There is no need for elevated temperatures for the process of the invention, but the invention is not limited to specific temperature, except by the boiling point of the selected liquid solvent as an upper limit.

In the most preferred embodiments of the invention we contact a feed gas comprising isocyanic acid in gaseous state with the liquid solvent. The step of absorbing the isocyanic acid gas can be carried out in any gas-liquid contacting apparatus that is suitable for the use. Elaborate apparatus is not necessary to obtain the advantages of the invention. The absorption can be carried out in a batch reactor simply by bubbling the gas into the solvent. Since the trimerization is rapid and the product precipitates, the bubbling in of the feed gas can be continued until any desired amount of product has been made, whereupon the gas feed is stopped and the solid product is separated. The process of the invention is readily adaptable for use in continuous processing apparatus. The liquid solvent is circulated through a gas-liquid contacting absorption column, preferably counter-current to the gas feed stream which contains the cyanic acid gas. The solvent taken from the absorber will contain the product solids in slurry which may be separated by filtration or the like. The solvent is then recirculated to the absorber. The circulating liquid may be cooled as necessary. The rate of absorption is rapid so that practically complete absorption can be readily accomplished by a single pass when using an absorber of sufficient absorption capacity.

We prefer to operate the invention with a catalyst (accelerator) in the liquid solvent for the trimerization. Only a catalytic amount is necessary and we find it convenient to operate with about one percent by weight of tributylamine in the liquid phase. When the selected solvent is a tertiary amine, or pyridine, it can serve both functions.

A preferred class of catalysts is the tertiary amines and our most preferred catalyst is tributylamine. Other catalysts that might be found useful in variations of the invention include sodium hydroxide, sodium methoxide, sodium acetate, lithium oxide, sodium formate, sodium carbonate, sodium benzoate, sodium borohydride, potassium tert-butoxide, calcium acetate, lead oleate, metal naphthenates, titanium tetra butyrate, Friedl-Crafts catalysts, oxalic acid, pyridine, triethyl phosphine, chloride salts, etc.

A convenient source of gaseous isocyanic acid for use in the process of this invention is the product gas stream taken from a process for catalytic oxidation of HCN with oxygen (e.g. air) over a metal catalyst such as silver, gold or the like. The catalytic oxidation of HCN was described in German Pat. Nos. 1,040,521 and 1,056,101. By selection of reaction conditions most preferable to cyanic acid selectivity, and by operating the oxidation reactor at temperatures higher than those described by the German patents, e.g. at 750° C. and by using 0.5 or more moles $O_2$ per mole HCN in the feed, with the feed rate adjusted for maximum HCN conversion, we are able to obtain 90 to 100% HCN conversion with about 80% selectivity of conversion to isocyanic acid. The product stream from this HCN oxidation reactor is a mixed gas stream consisting essentially of isocyanic acid with by-products and unreacted feed gases, i.e. cyanogen, CO, $CO_2$, HCN, $O_2$, $N_2$, $H_2O$, etc. Isocyanic acid from other sources can be used instead. A suitable mixture is the product containing nitric oxide and isocyanic acid from the synthesis of isocyanic acid from nitric oxide described at SCIENCE, Vo. 202, p 525 (Nov. 1978). See also U.S. Pat. No. 4,174,377. Japan Patent Application No. 49-7000 describes isocyanic acid of 99% purity from pyrolysis of urea.

Some of the impurities in the feed gas stream may be soluble in the solvent that is used to absorb the isocyanic acid, but none should be reactive, to appreciable extent, particularly not to form insoluble products, so that all of the feed gas impurities will be effectively separated by the absorption and trimerization of the cyanic acid component. One may use pure isocyanic acid as the feed to the absorber in the process of the invention, but it may be preferred to use isocyanic acid feed with diluent gases that will not form precipitates. A diluent such as $N_2$ or $O_2$ or Argon for example may be advantageous to cool the liquid thus removing heat of reaction for temperature control. Diluent gas in the feed may be also desirable to assist in dispersing the isocyanic acid in the liquid for more even absorption.

The invention can be carried out at essentially atmospheric pressure in the absorber. We may operate the absorber under higher pressures to reduce loss by evaporation of the solvent or to improve the absorption rate, but this has not been necessary in our most preferred embodiments.

Detailed examples which include our presently most preferred mode of carrying out the invention follow:

EXAMPLE 1

In one experimental laboratory trimerization a gas with the following approximate composition was fed continuously to the gas-liquid contacting equipment:

| | |
|---|---|
| HNCO | 13.5% by vol. |
| $N_2$ | 82.5% |
| $O_2$ | 0.2% |
| HCN | 0.7% |
| CO | 0.6% |
| $CO_2$ | 2.6% |
| $(CN)_2$ | 0.01% |

The total gas flow rate was about 3.65 g. moles/hr.

The gas was fed into and flowed upwards for a single pass through a glass column approximately 13" high×1" in diameter. A solution of 2.5 g tributylamine and 213 g acetonitrile was circulated downward through the column. When this liquid exited at the bottom of the column, a centrifugal pump recirculated it back to the top of the column. A portion of this recirculated solution could be passed through a sintered stainless filter prior to reentering the absorber-reactor. A few minutes after this system was started up, white solids could be seen in the recirculating liquid. After 3.2 minutes, a portion of the liquid was started through the filter. This was continued until 60 minutes after start, then the feed gas was stopped. The filter cake was scraped off the filter and dried. 9.1 Grams of dry solids containing 92% pure cyanuric acid was recovered.

EXAMPLE 2

In another experiment using the same recirculating system described in Example 1 but with no filtration, a liquid solution of 99 g acetonitrile and 1 g of tributylamine was circulated. A gas stream of similar composition to that in Example 1 was fed to the glass column for 11.5 minutes at a rate differing slightly from that in Example 1. The resulting slurry was then filtered. The solid product after drying weighed 3.4 g and contained 99% cyanuric acid. The yield of solids based on the HNCO feed in the experiment was 97%.

EXAMPLE 3

In another experiment, another HNCO containing gas stream of composition similar to that described in Example 1 was bubbled into a stirred liquid solution in a flask containing 200 g of o-dichlorobenzene and 8 g of tributylamine. After 30 minutes of absorption and reaction at 30° C., the slurry was filtered and the solid product was dried. 12.2 Grams of dry solids containing 90% cyanuric acid was recovered (a 100% yield of solids based on the HNCO absorbed).

EXAMPLE 4

In one experimental laboratory trimerization a gas with the following approximate composition was fed continuously to the equipment:

| | |
|---|---|
| HNCO | 9.9% by vol. |
| $N_2$ | 81.7% |
| $O_2$ | 1.0% |
| HCN | 3.5% |

| | |
|---|---|
| CO | .03% |
| CO$_2$ | 1.9% |
| (CN)$_2$ | 2.0 |

The total gas flow rate was about 3.1 g moles/hr.

The gas bubbled into a stirred liquid solution consisting of 200 g of acetonitrile and 2 g of tributylamine in a flask. The liquid temperature was maintained at 20° C. After several minutes solids could be seen in the liquid. After 45 minutes the feed gas was stopped, the slurry was filtered, and the solids product was dried. 7.2 Grams of dry solids containing 93% cyanuric acid was recovered (a 73% yield of solids based on HNCO fed). It is expected that improved gas-liquid contacting would improve the solids yield.

EXAMPLE 5

In another experiment that was conducted in exactly the same manner as in Example 4 except the fed gas composition was

| | | |
|---|---|---|
| HNCO | 9.4% | by vol. |
| N$_2$ | 81.3 | |
| O$_2$ | 0.6 | |
| HCN | 5.2 | |
| CO | 0.1 | |
| CO$_2$ | 2.1 | |
| (CN)$_2$ | 1.3 | |

The total gas flow rate was about 3.1 g moles/hr.

7.4 Grams of dry solids containing 92% cyanuric acid was recovered (a 78% yield of solids based on HNCO fed).

In Table I, several liquid organic solvents are listed in order of descending values of their respective dielectric constants, shown in the center column. In the right hand column, opposite each solvent, are shown the product purities of solids products separated from the liquid mediums in experimental processes like those described in Examples 2 and 3 using the several tabulated solvents as the liquid mediums. Where several values are shown, each represents a separate experimental run using the designated solvent composition. Results marked with an asterisk in the table indicate a separate catalyst was not used.

TABLE I
TRIMERIZATION OF HNCO
(at 25–40° C., using 1% Tributylamine Catalyst)

| Solvent | Dielectric Constant | Product Purity % Cyanuric Acid in Solid |
|---|---|---|
| Acetonitrile | 39 | 97, 99, 97, 99 |
| Amyl Acetate | 25 | 94, 93, 94 |
| Cyclohexanone | 18 | 95, 98, 94 |
| Acetophenone | 17 | 95, 94 |
| Pyridine | 12.3 | 80* |
| o-Dichlorobenzene | 10 | 87 |
| Dimethoxyethane | 7.2 | 97 |
| Chlorobenzene | 6 | 89, 83 |
| n-Butylacetate | 5 | 57 |
| o-Chlorotoluene | 4.5 | 67 |
| Diethylether | 4.3 | 56 |
| Xylene (mixed) | 2.4 | 61 |
| Toluene | 2.4 | 59, 68 |
| Tributylamine approx. | 2.2 | 56* |
| Cyclohexane | 2.0 | 37 |

EXAMPLE 6

In another experiment, 3.65 moles per hour of a gas mixture containing 13.3 volume % HNCO and 1.5 volume % NO was bubbled into a stirred liquid in a flask containing 200 g of acetonitrile plus 2 g of tributylamine. After 30 minutes of absorption and reaction at 30° C., the slurry was filtered and the solid product was dried. 11.1 Grams of dry solids containing 93% cyanic acid was recovered.

EXAMPLE 7

The gaseous effluent containing cyanic acid produced by the decomposition of urea using the technique described in Japanese Patent Application No. 49-7000 (1974) is bubbled into a stirred flask containing a solution of 1% tributylamine in acetonitrile. Cyanuric acid of greater than 99% purity is produced in 99% yield.

In all of the foregoing examples the isocyanic acid was contacted in gaseous state with the liquid reaction medium. We have also contacted isocyanic acid in liquid state by adding the liquid reactant slowly to the organic liquid solvent medium with constant agitation as by stirring. Under these circumstances the results are about the same as when the isocyanic acid is contacted in gaseous state with the liquid solvent.

We claim:

1. A process of making cyanuric acid which comprises adding isocyanic acid to a liquid organic solvent for isocyanic acid in which solvent said isocyanic acid when absorbed will undergo trimerization reaction to produce cyanuric acid which will precipitate from said solvent, said liquid organic solvent being a polar solvent having dielectric constant greater than 5.

2. A process defined by claim 1 wherein said isocyanic acid is added by contacting gas comprising gaseous isocyanic acid with the defined liquid organic solvent.

3. A process defined by claim 1 wherein said polar solvent has a dielectric constant greater than 15.

4. A process defined by claim 2 wherein said gas comprising isocyanic acid further comprises inert gas diluents.

5. A process defined by claim 1 wherein the defined organic solvent is acetonitrile.

6. A process defined by claim 2 wherein said contacting is carried out in a continuous gas-liquid contacting apparatus with circulation of the liquid solvent countercurrent to a continuous stream of the gas comprising cyanic acid in said apparatus.

7. A process defined by claim 6 wherein solid product comprising cyanuric acid is separated from said liquid solvent during recirculation of said liquid to said apparatus.

8. A process defined by claim 2 further comprising a step of separating solid product comprising cyanuric acid from said organic solvent.

9. A process defined by claim 8 wherein said solid product consists of at least 90 percent by weight cyanuric acid.

10. A process defined by claim 1 wherein said liquid organic solvent comprises a catalyst for the trimerization of isocyanic acid.

11. A process defined by claim 10 wherein said catalyst is a tertiary amine.

12. A process defined by claim 11 wherein the defined catalyst is tributylamine.

13. A process defined by claim 1 wherein the total solid precipitate from said solvent consists of at least 90 percent by wt. of cyanuric acid.

14. A process defined by claim 4 wherein the inert gas comprises at least one member selected from the group consisting of nitrogen, argon, cyanogen and nitric oxide.

15. A process defined by claim 1 wherein a solid product is obtained consisting of at least 90% by wt. cyanuric acid and the yield of solids based on HNCO fed is at least 90%.

* * * * *